US011291637B2

(12) United States Patent
Krishnan et al.

(10) Patent No.: US 11,291,637 B2
(45) Date of Patent: Apr. 5, 2022

(54) METHODS FOR TREATING OR PREVENTING ORGANOPHOSPHATE POISONING

(71) Applicant: The Henry M. Jackson Foundation for the Advancement of Military Medicine, Inc., Bethesda, MD (US)

(72) Inventors: Jishnu K. S. Krishnan, Bethesda, MD (US); Aryan M. Namboodiri, Gaithersburg, MD (US); John R. Moffett, North Potomac, MD (US); Peethambaran Arun, Clarksburg, MD (US); Narayanan Puthillathu, Rockville, MD (US); Ranjini Vengilote, Rockville, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 0 days.

(21) Appl. No.: 16/333,685

(22) PCT Filed: Sep. 18, 2017

(86) PCT No.: PCT/US2017/052008
§ 371 (c)(1),
(2) Date: Mar. 15, 2019

(87) PCT Pub. No.: WO2018/053397
PCT Pub. Date: Mar. 22, 2018

(65) Prior Publication Data
US 2019/0231713 A1    Aug. 1, 2019

Related U.S. Application Data

(60) Provisional application No. 62/395,472, filed on Sep. 16, 2016.

(51) Int. Cl.
| | |
|---|---|
| *A61P 39/02* | (2006.01) |
| *A61K 31/02* | (2006.01) |
| *A61K 9/00* | (2006.01) |
| *A61K 31/08* | (2006.01) |
| *A61K 33/00* | (2006.01) |
| *A61P 39/00* | (2006.01) |
| *A61K 45/06* | (2006.01) |

(52) U.S. Cl.
CPC ............ *A61K 31/08* (2013.01); *A61K 9/0043* (2013.01); *A61K 31/02* (2013.01); *A61K 33/00* (2013.01); *A61P 39/02* (2018.01); *A61K 45/06* (2013.01); *A61P 39/00* (2018.01)

(58) Field of Classification Search
None
See application file for complete search history.

(56) References Cited

U.S. PATENT DOCUMENTS

| 2009/0023706 A1 | 1/2009 | Albuquerque et al. |
| 2011/0064716 A1* | 3/2011 | Soreq .................. A61K 38/465 |
| | | 424/94.6 |

FOREIGN PATENT DOCUMENTS

| WO | 94/22306 A1 | 10/1994 |
| WO | 2014/142548 A1 | 9/2014 |

OTHER PUBLICATIONS

Hamilton, M.G., et al., Clinical Aspects of Percutaneous Poisoning by the Chemical Warfare Agent VX: Effects of Application Site and Decontamination, Military Medicine, 169, 11:856, 2004.*
Testylier, G., et al., Cerebral edema induced in mice by a convulsive dose of soman. Evaluation through diffusion-weighted magnetic resonance imaging and histology, Toxicology and Applied Pharmacology 220 (2007) 125-137.*
Sawyer, T.W., et al., Non-cholinergic intervention of sarin nerve agent poisoning, Toxicology 294 (2012) 85-93.*
Hamilton et al., "Clinical Aspects of Percutaneous Poisoning by the Chemical Warfare Agent VX: Effects of Applicatino Site and Decontamination", Military medicine, 169: 856-862 (2004).
Chilcott et al., "Evaluation of a Barrier Cream against the Chemical Warfare Agent VX using the Domestic White Pig", Basic & Clinical Pharmacology & Toxicology, 97: 35-38 (2005).
Krishnan et al., "Brief isoflurane administration as a post-exposure treatment for organophosphate poisoning", Neurotoxicology, 1-2 (2017).
International Search Report issued in corresponding International Patent Application No. PCT/US2017/052008, (dated 2017).
European Written Opinion & Search Report dated May 25, 2020, from corresponding EP Patent Application No. 17851696.9, 6 pages.
Grasshoff et al., "Effects of cholinergic overstimulation on isoflurane potency adn efficacy in cortical and spinal networks," Toxicology, Limerick, IR, vol. 229, No. 3, Dec. 20, 2006 (Dec. 20, 2006), pp. 206-213, XP005809577, ISSN: 0300-483X, DOI: 10.1016/J.Tox. 2006.10.017, 6 pages.

* cited by examiner

*Primary Examiner* — H. Sarah Park
(74) *Attorney, Agent, or Firm* — Lee & Hayes, P.C.

(57) ABSTRACT

The invention relates to methods of treating or preventing organophosphate poisoning in a subject in need thereof, comprising administering to the subject isoflurane, enflurane, halothane, sevoflurane, desflurane, xenon or argon in a therapeutically effective amount.

15 Claims, 8 Drawing Sheets

METHODS FOR TREATING OR PREVENTING ORGANOPHOSPHATE POISONING

CROSS REFERENCE TO RELATED APPLICATIONS

The present application is a U.S. National Phase Application of International Application No. PCT/US2017/052008, filed Sep. 18, 2017, which claims the benefit of U.S. Provisional Application No. 62/395,472, filed Sep. 16, 2016, both of which are hereby incorporated by reference in their entirety.

STATEMENT REGARDING FEDERALLY SPONSORED RESEARCH OR DEVELOPMENT

This invention was made with government support under Grant No. NS 076448 awarded by the National Institutes of Health. The Government has certain rights in the invention.

BACKGROUND OF THE INVENTION

Field of the Invention

The invention relates to methods of treating or preventing organophosphate poisoning in a subject in need thereof, comprising administering to the subject at least one halogenated anesthetic in a therapeutically effective amount.

Background of the Invention

Organophosphate poisoning is a significant world health problem, claiming thousands of lives per year through intentional and unintentional pesticide exposure. Potential for a terrorism based release scenario has made the situation worse. Organophosphate based chemical threat agents (CTA) exert their toxic effects through cholinergic overactivation during the initial phase. If not treated immediately, however, a shift to a glutamatergic phase can lead to status epilepticus (SE), irreversible neuronal degeneration and long term CNS damage. Prognosis for any CTA-based post exposure treatment is poor since most drugs fail to inhibit the post exposure phase of non-cholinergic activation. The efficacy of delayed treatments against OP-CTA toxicity is limited due to the fact that most drugs fail to inhibit the later phase of non-cholinergic activation. For example, the current Food and Drug Administration approved anticonvulsant treatment for OP-CTA poisoning, diazepam, loses effectiveness if treatment is delayed (Apland (2014) J. Pharmacol. Exp. Ther. 351, 359-372).

The potential use of anesthetics as neuroprotectants in nerve agent poisoning has been shown in several earlier studies. In one study, sub-anesthetic doses of ketamine were found to stop ongoing seizures when administered 30 minutes after soman challenge (Dorandeu (2005) Brain Res. 1051, 164-175). An extended delay before treatment of up to 2 hours required an increase in ketamine dose that reached the anesthetic dose level. In another study, anesthesia using isoflurane maintained for 1.5 hours during diffusion-weighted magnetic resonance imaging interrupted soman-induced seizures and attenuated edema in selected brain areas in mice (Testylier (2007) Toxicol. Appl. Pharmacol. 220, 125-137). In a later study the protective effects of several anesthetics on sarin poisoning were investigated in domestic swine (Sawyer (2012) Toxicology 294, 85-93). In this study 2% isoflurane was delivered in 100% oxygen continuously for 6 hours and resulted in profound protection against sarin poisoning. Again, a longer duration of 1 hour isoflurane administration was used in these studies, raising the possibility for long term toxicity by isoflurane. None of the investigations examined shorter duration isoflurane administration.

SUMMARY OF THE INVENTION

The invention relates to methods of treating or preventing organophosphate poisoning in a subject in need thereof, comprising administering to the subject at least one halogenated anesthetic in a therapeutically effective amount.

The invention encompasses a method of treating or preventing organophosphate poisoning in a subject in need thereof, comprising administering to the subject isoflurane, enflurane, halothane, sevoflurane, desflurane, xenon or argon in a therapeutically effective amount. In some embodiments, the isoflurane, enflurane, halothane, sevoflurane, desflurane, xenon or argon is administered intranasally.

In some embodiments, the subject was exposed to an organophosphate poisoning prior to administration of the isoflurane, enflurane, halothane, sevoflurane, desflurane, xenon or argon. In some embodiments, the subject was exposed to the organophosphate at least about 5 minutes prior to the administration of the isoflurane, enflurane, halothane, sevoflurane, desflurane, xenon or argon. In some embodiments, the subject was exposed to the organophosphate between about 5 minutes and about 120 minutes prior to the administration of the isoflurane, enflurane, halothane, sevoflurane, desflurane, xenon or argon. In some embodiments, the subject was exposed to the organophosphate between about 10 minutes and about 60 minutes prior to the administration of the isoflurane, enflurane, halothane, sevoflurane, desflurane, xenon or argon. In some embodiments, the organophosphate is sarin, soman, cyclosarin, VX, paraoxon, or tabun.

In some embodiments of the methods of the invention, the isoflurane, enflurane, halothane, sevoflurane, desflurane, xenon or argon is administered to the subject for about 10 minutes or less, including but not limited to, about 1 to about 8 minutes, or about 2 to about 6 minutes. In some embodiments, the isoflurane, enflurane, halothane, sevoflurane, desflurane, xenon or argon is administered to the subject for at least 4 minutes.

In some embodiments of the methods of the invention, the isoflurane, enflurane, halothane, sevoflurane, desflurane, xenon or argon is administered to the subject at a concentration of about 0.5% to about 7%, or about 1% to about 5%. In some embodiments, the isoflurane, enflurane, halothane, sevoflurane, desflurane, xenon or argon is administered to the subject at a concentration of about 4.5% to about 5%, for about 5 minutes wherein the subject was exposed to the organophosphate between about 30 minutes and about 60 minutes prior to said administration.

In some embodiments of the methods of the invention, the concentration of the isoflurane, enflurane, halothane, sevoflurane, desflurane, xenon or argon is increased during administration to the subject. In some embodiments, the concentration of the isoflurane, enflurane, halothane, sevoflurane, desflurane, xenon or argon is increased during administration such that the subject is exposed for about 1 minute or less to the highest concentration of isoflurane, enflurane, halothane, sevoflurane, desflurane, xenon or argon administered.

In some embodiments of the methods of the invention, the isoflurane, enflurane, halothane, sevoflurane, desflurane, xenon or argon is co-administered with at least one oxime. In some embodiments, isoflurane is administered to the subject. In some embodiments, the isoflurane, enflurane, halothane, sevoflurane, desflurane, xenon or argon is co-administered with oxygen. In some embodiments, the oxygen is administered to the subject at a concentration of about 90% to about 99%.

DETAILED DESCRIPTION OF THE INVENTION

Figure 1:
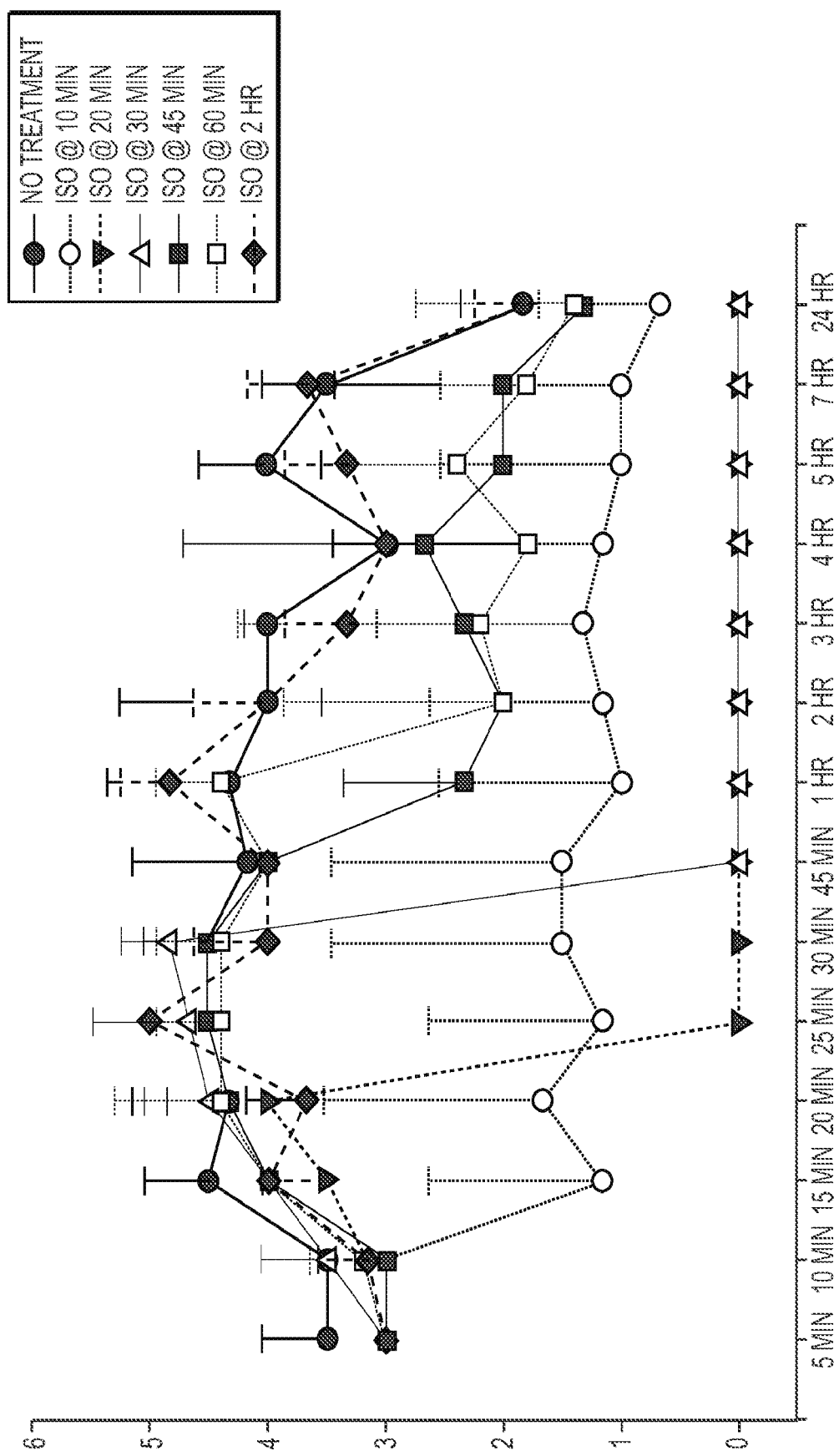
FIG. 1 depicts the seizure activity in the rats in a time course study. Values are means+SD with n=6 for each group except for the group given isoflurane briefly at 1 hour post-paraoxon, where n=5. Animals given isoflurane at 10 minutes post-paraoxon intoxication continued moderate seizure activity throughout the course of the study, whereas rats administered isoflurane at 20 minutes (light blue line) and 30 minutes (green line) immediately stopped seizure activity for the remainder of the observation period. Rats given isoflurane at 10 minutes and 45 minutes or later also continued moderate to severe seizure activity for the remainder of the observation period.
Figure 2B:
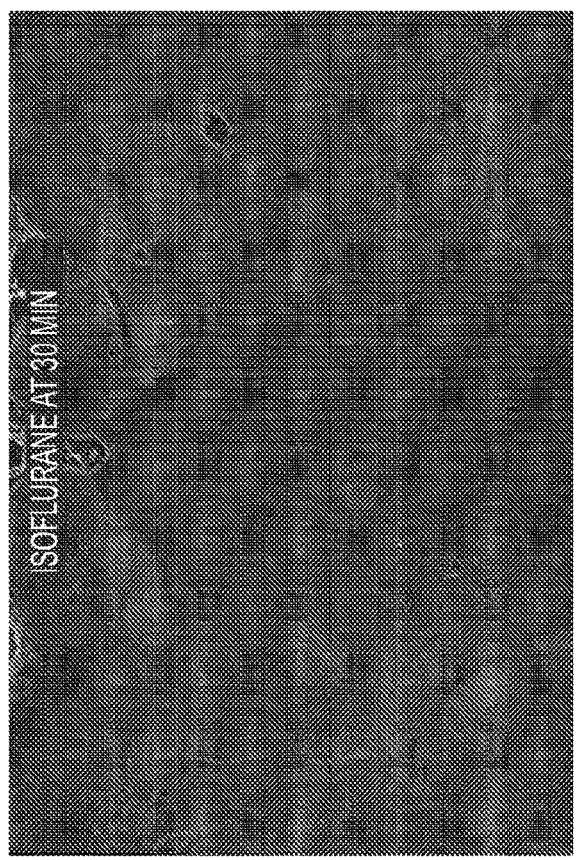
FIG. 2 depicts the neuropathology in untreated and isoflurane treated animals using FJC staining. The area shown in both images is central thalamus. Extensive neuronal loss was observed in paraoxon intoxicated untreated animals as shown by staining with FJC at 24 hours (2A). Isoflurane administered briefly 30 minutes after paraoxon treatment prevented the neurodegeneration observed in untreated rats (2B; n=6 per group).
Figure 2A:
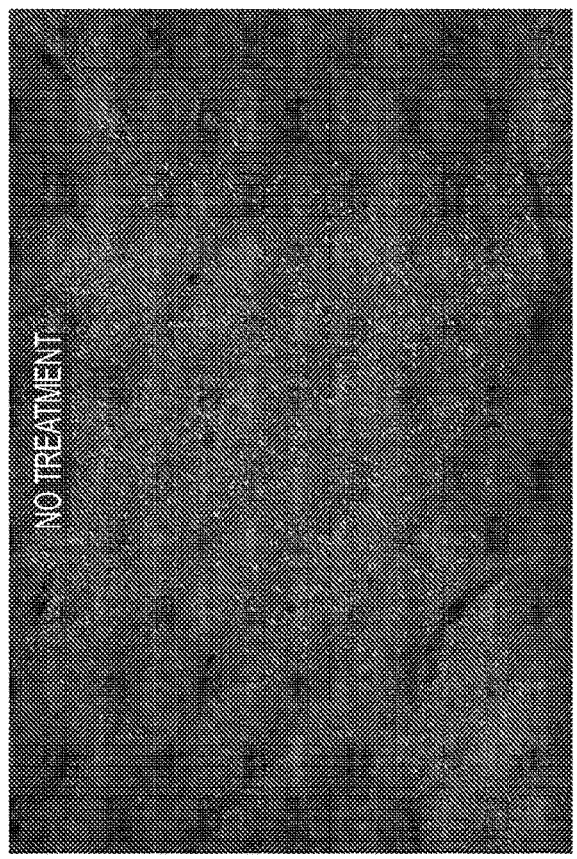
Figure 3B:
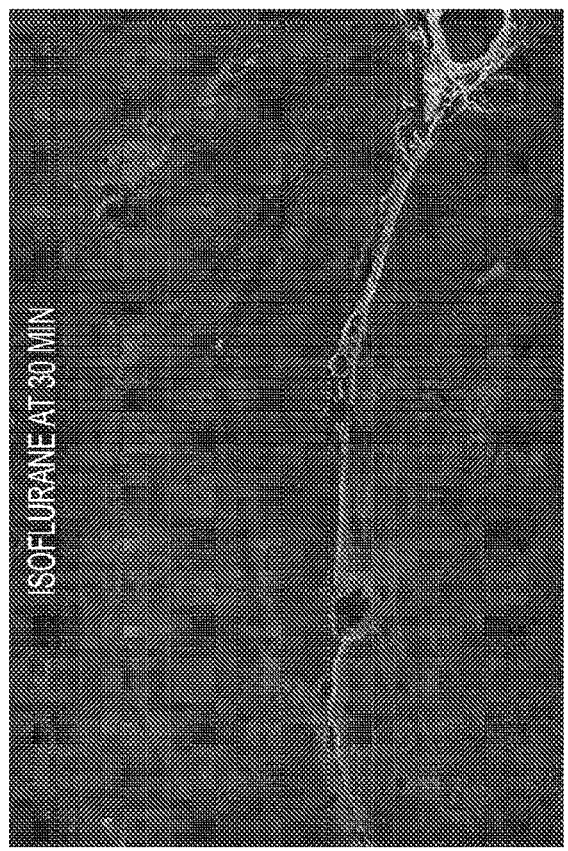
FIG. 3 depicts FJC staining for neuronal loss in hippocampus and dorsolateral thalamus. In the majority of untreated rats, neuronal loss as shown by FJC staining was extensive in the hippocampus and dorsolateral thalamus (2A). In rats treated briefly with isoflurane 30 minutes after paraoxon intoxication, the neuronal loss was prevented (2B).
Figure 3A:
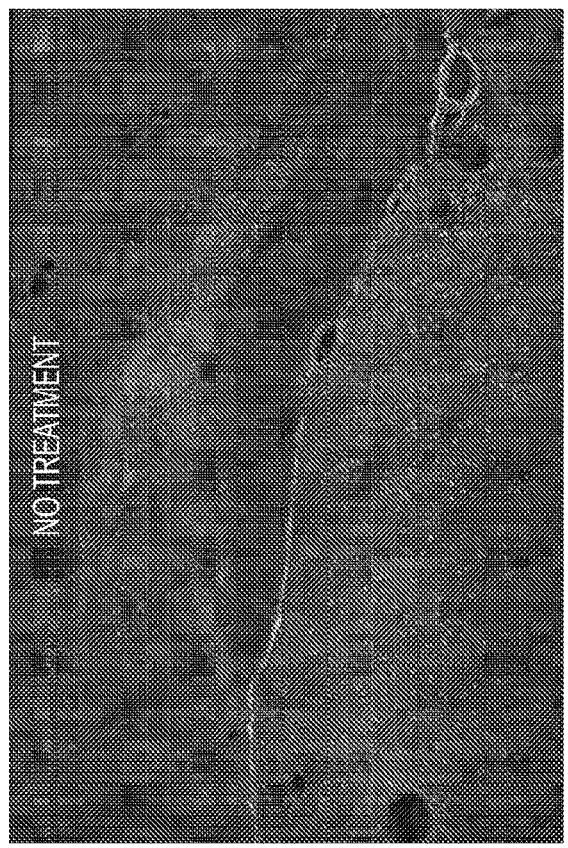
Figure 4B:
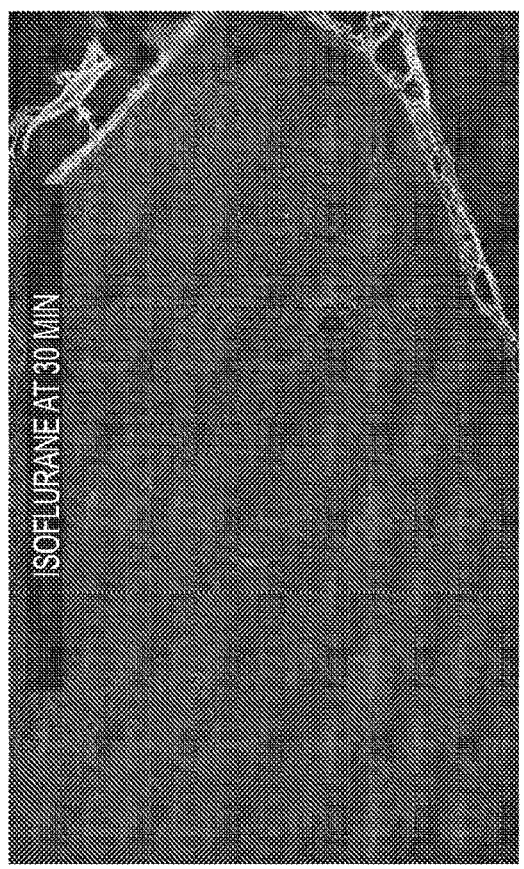
FIG. 4 depicts FJC staining for neuronal loss in the medial cortical amygdala. Neuronal loss was extensive in untreated rats as shown by FJC staining in several areas associated with the piriform cortex, including several nuclei in the amygdala, e.g., medial cortical amygdala (2A). Staining was not seen in the same region in rats that were treated briefly with isoflurane 30 minutes after paraoxon administration (2B).
Figure 4A:
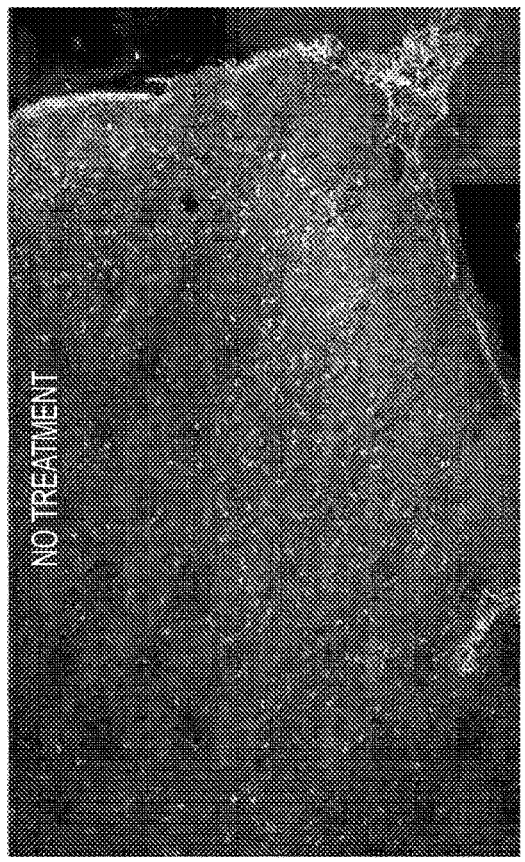
Figure 5:
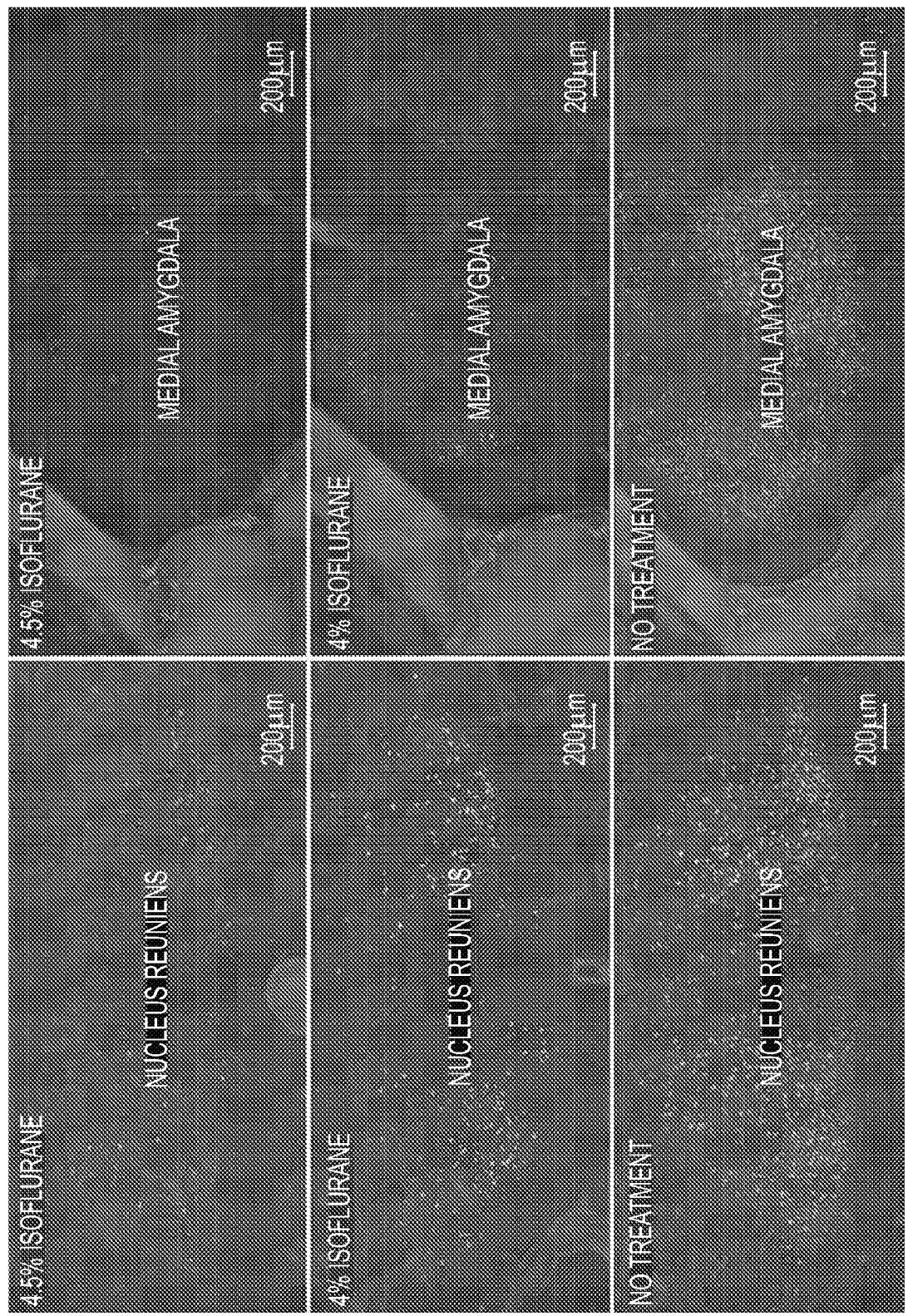
FIG. 5 depicts Fluoro Jade B (FJB) staining for degenerating neurons 24 hours after paraoxon administration. In animals that were not treated with isoflurane, moderate to extensive neurodegeneration was observed in areas such as the nucleus reuniens of the central thalamus and the medial amygdala. Animals exposed to 4% isoflurane for 5 minutes one hour after paraoxon administration had significantly reduced neurodegeneration. Animals exposed to 4.5% isoflurane for 5 minutes one hour after paraoxon administration had minimal neurodegeneration at the 24 hour time point.

The invention relates to methods of treating or preventing organophosphate poisoning in a subject in need thereof, comprising administering to the subject at least one halogenated anesthetic in a therapeutically effective amount.

As used herein, the terms "treat" or "treating" refer to an amelioration of at least one discernible symptom associated with organophosphate poisoning. The term "treat" can be used in the context of a subject that has been exposed to or is suspected of having been exposed to an organophosphate, prior to the onset of any discernable or measurable symptom thereof. Organophosphates are known to inactivate acetylcholinesterase (AChE); thus, in one embodiment of the invention, the methods can be used to treat inactivated of AChE. In one specific embodiment, the methods can be used to treat AChE inactivation. For example, the term treat can mean administering at least one halogenated anesthetic to a subject that was exposed to or suspected of being exposed to a nerve toxin, such as sarin, prior to the onset of any noticeable symptom of sarin poisoning. In yet another embodiment, "treatment" or "treat" refers to delaying the onset of a physical parameter or symptom of inactivated AChE. As used herein, the term "halogenated anesthetic" refers to isoflurane, enflurane, halothane, sevoflurane or desflurane. As used herein, the term "noble gas" refers to xenon or argon. In specific embodiments, the halogenated anesthetic is isoflurane.

When administration is for the purposes of "preventing" or interfering with organophosphate poisoning ("prophylactic administration"), the at least one halogenated anesthetic or noble gas is provided in advance of any visible or detectable symptom. The prophylactic administration of at least one halogenated anesthetic or noble gas serves to attenuate subsequently arising symptoms or physical parameters or reduce the possibility of symptoms from arising altogether. Thus, as used herein, the term "prevent," as used in connection with administering at least one halogenated anesthetic or noble gas, is used to indicate the timing of the administration, i.e., before a detectable symptom arises, rather than indicate a complete removal of the possibility of developing any symptoms associated with organophosphate poisoning. The term "prevent" can thus also mean that administration of the at least one halogenated anesthetic or noble gas are intended to "reduce the likelihood" that a symptom of organophosphate poisoning will appear or become detectable.

As used herein, AChE toxicity is well-understood in the art and is intended to mean inhibition of the activity of AChE. Typically, AChE is found in chemical synapses and neuromuscular junctions in an "active" state. AChE catalyzes the breakdown of acetylcholine to acetate and choline to block the action of acetylcholine on its receptors. Certain compounds, however, such as but not limited to nerve toxins and pesticides can inactivate AChE. For example, organophosphorous compounds can form a covalent adduct with AChE thereby preventing AChE from functioning to block the action of acetylcholine. If left untreated, exposure to organophosphates can result in neurological damage, loss of muscle function and even death.

Organophosphates are thought to affect the activity of AChE in a two-stage process. First, the organophosphate compounds can form a covalent adduct with the enzyme, thereby immediately inhibiting the function of AChE. Once deactivated, the AChE enzyme then undergoes a dealkylation reaction known as "aging." This dealkylatyion reaction is considered irreversible, thereby rendering the aged AChE as non-functional. Without being bound by theory, it is thought that administration of at least one halogenated anesthetic or noble gas according to the methods of the present invention is useful in preventing the aging of AChE and/or reversing the reversing the formation of the covalent adduct that the organophosphate forms with AChE. Accordingly, the phrase "preventing the deactivation of acetylcholinesterase" or "interfering with the deactivation of acetylcholinesterase" are used herein to mean that administration of the at least one halogenated anesthetic or noble gas can be used to prevent or interfere with the dealkylation of AChE that has been or could be exposed to an inactivating compound, such as but not limited to an organophosphate, thereby preventing the "aging" or permanent inactivation of AChE. It is thus not necessary that the subject would have been previously exposed to an AChE inactivating compound to perform methods of preventing or interfering with the deactivation of AChE. As used herein, acetylcholinesterase, or AChE, includes active AChE, covalently inactivated AChE or aged AChE. Moreover, "inactive AChE" includes covalently inactivated AChE or aged AChE.

Examples of AChE inactivating agents include but are not limited to sarin, cyclosarin, tabun, soman and V-agents such as but not limited to VX and VR and organophosphate pesticides such as paraoxon. It is understood that being exposed to an inactivating agent also means being exposed to a compound that is metabolized into an AChE inhibitor. For example, a subject that is exposed to the compound parathion is considered, for the purposes of this invention, to having been exposed to paraoxon, as it is well-known that paraoxon is the active metabolite of parathion. The invention is not limited to the specific AChE inhibitor to which the subject is exposed.

The invention thus provides methods of treatment and prophylaxis by administration of a therapeutically effective amount of at least one halogenated anesthetic or noble gas to a subject in need thereof. The terms patient and subject are used interchangeably herein and can be a mammal, including, but not limited, to an animal such as a cow, horse, sheep, pig, cat, dog, mouse, rat, rabbit, guinea pig, etc. and a human or non-human primate. As used herein, the phrase "a subject in need therein" refers to a subject that has knowingly been exposed to an organophosphate or an agent that causes AChE toxicity or is suspected of having been exposed to an oprganophosphate or an agent that causes AChE toxicity. In one embodiment, a subject that is "suspected" of having been exposed an organophosphate or an agent that causes AChE toxicity is a subject that is exhibiting one or more discernible symptoms of organophosphate poisoning and/or AChE toxicity, even if the identity of the toxic agent to which the subject was exposed is unknown. In another embodiment, a subject that is "suspected" of having been exposed to an organophosphate or an agent that causes AChE toxicity is a subject that has been in close proximity to an organophosphate or an AChE inhibitor such that the chances of exhibiting one or more discernible symptoms of AChE toxicity is increased, even if the subject has not yet started exhibiting symptoms of organophosphate poisoning and/or AChE toxicity.

As used herein, the term "administer" or "administering" is used to mean introducing at least one halogenated anesthetic or noble gas to the subject such that the at least one halogenated anesthetic, e.g., isoflurane, or noble gas, e.g., xenon, can exert a biological effect, such as but not limited to acting on AChE. Typically, the halogenated anesthetic or noble gas are gases and are administered intranasally such that the subject simply inhales the halogenated anesthetic or noble gas, either consciously or unconsciously, to allow the halogenated anesthetic or noble gas to reach the subject's lungs, which then enters the blood stream and reaches the subject's brain. Thus, the term "intranasal" does not imply or require direct insertion of a delivery device into the nostril of a subject. In another embodiment, the halogenated anesthetic or noble gas is administered to the subject though the mouth or oral cavity ("intraorally") or even through the trachea. For example, the halogenated anesthetic or noble gas can be administered by having a subject breath through its mouth such that the halogenated anesthetic or noble gas passes through the oral cavity and reaches the subject's lungs and ultimately the subject's brain.

Of course, "administration" can also include administering a combination of compounds. Thus, administration may be in the form of dosing an organism with the halogenated anesthetic or noble gas and an additional compound, such that the organism's circulatory system will deliver the at least one halogenated anesthetic or noble gas and/or additional compound to the target area.

In select embodiments, a combination of compounds can be administered, thus the individual compounds can also be said to be co-administered with one another. As used herein, "co-administer" indicates that each of at least two compounds is administered during a time frame wherein the respective periods of biological activity or effects overlap. Thus the term co-administer includes sequential as well as coextensive administration of individual compounds, at least one of which is a halogenated anesthetic, such as isoflurane or noble gas, such as xenon. Likewise, the phrase "combination of compounds" indicates that the individual compounds are coadministered, and the phrase "combination of compounds" does not mean that the compounds must necessarily be administered contemporaneously or coextensively. In addition, the routes of administration of the individual compounds need not be the same.

In select embodiments, the halogenated anesthetic or noble gas is coadministered with an agent that will reactivate covalently inactivated AChE. Examples of agents that can reactivate covalently inactivated AChE, i.e., "rescue covalently inactivated AChE," include but are not limited to oximes and atropine sulphate. Examples of oximes that can be coadministered with at least one compound of the invention include but are not limited to 2-pralidoxime ("2-PAM") and 1-(2'-hydroxyiminomethyl-1'-pyridinium)-3-(4'-carbamoyl-1-pyridinium) ("HI-6"). In specific embodiments of the present invention, the halogenated anesthetic, e.g., isoflurane, or noble gas, e.g., xenon, may be administered with, before or after an agent that will reactivate covalently inactivated AChE. The co-administration of these compounds may be as a treatment or as a prophylactic administration.

In select embodiments of the methods of the present invention, the subject was exposed to an organophosphate prior to administration of the at least one halogenated anesthetic or noble gas. In a specific embodiment, the subject was exposed to an organophosphate between about 1 minute and about 120 minutes prior to the administration of the at least one halogenated anesthetic or noble gas. In more specific embodiments, the subject was exposed to an organophosphate between about 5 minutes and about 60 minutes prior to the administration of the at least one halogenated anesthetic or noble gas, between about 10 minutes and about 45 minutes prior to the administration of the at least one halogenated anesthetic or noble gas, between about 15 minutes and about 40 minutes prior to the administration of the at least one halogenated anesthetic or noble gas or between about 20 minutes and about 35 minutes prior to the administration of the at least one halogenated anesthetic or noble gas. In more specific embodiments, the subject was exposed to an organophosphate about 15 minutes prior, about 30 minutes prior, about 45 minutes prior or about 60 minutes prior to the administration of the at least one halogenated anesthetic or noble gas. In even more specific embodiments, the subject was exposed to an organophosphate about 15 minutes prior, about 30 minutes prior, about 45 minutes prior or about 60 minutes prior to the administration of isoflurane or xenon.

In other select embodiments, the at least one halogenated anesthetic or noble gas is administered to the subject for about 0.5 to about 10 minutes. In other words, when the halogenated anesthetic or noble gas is administered intranasally, intraorally or intratracheally to the subject the halogenated anesthetic or noble gas is included in the gas that is being inhaled into the lungs for a specified time. In more specific embodiments, the halogenated anesthetic or noble gas is administered to the subject for about 1 to about 8 minutes or for about 2 to about 6 minutes. In a more specific embodiment, the at least one halogenated anesthetic or noble gas is administered to the subject for about 4 minutes. In an even more specific embodiment, isoflurane is administered to the subject for about 4 minutes.

As used herein and unless otherwise indicated, the phrase "therapeutically effective amount" of the halogenated anesthetic or noble gas is measured by the therapeutic effectiveness of the halogenated anesthetic or noble gas, wherein at least one adverse effect of organophosphate poisoning is ameliorated, alleviated reduced or prevented. In specific embodiments, the at least one halogenated anesthetic or noble gas is administered to the subject at a concentration of about 0.5% to about 7%. As used herein, the concentration of the halogenated anesthetic or noble gas is measured as a percentage of the halogenated anesthetic or noble gas in relation to it environment. For example, if isoflurane is being administered as a gas at a concentration of 3.5%, the mix gas mixture contains 3.5 parts isoflurane and 96.5 parts additional gas. These additional gases may be air or otherwise pure oxygen. In more specific embodiments, the at least one halogenated anesthetic or noble gas is administered to the subject at a concentration of about 1% to about 6%, about 2% to about 5% or about 3% to about 4%. In more specific embodiments, isoflurane or xenon is administered to the subject at a concentration of about 1% to about 6%, about 2% to about 5%, about 3% to about 4% or about 4% to about 5%. In even more specific embodiments, isoflurane or xenon is administered to the subject at a concentration of about 1%, about 1.5%, about 2%, about 2.5%, about 3%, about 3.5%, about 4%, about 4.5% or about 5%. In more specific embodiments, at least one halogenated anesthetic or noble gas is administered to the subject at a concentration of about 4.5% to about 5%, wherein the subject was exposed to an organophosphate about 15 minutes prior, about 30 minutes prior, about 45 minutes prior or about 60 minutes prior to the administration of the at least one halogenated anesthetic or noble gas. In more specific embodiments, isoflurane or xenon is administered to the subject at a concentration of about 4.5% to about 5%, wherein the subject was exposed to an organophosphate about 15 minutes prior, about 30 minutes prior, about 45 minutes prior or about 60 minutes prior to the administration of isoflurane or xenon.

In other specific embodiments, concentration of the at least one halogenated anesthetic or noble gas is increased during administration to the subject. The increase can be gradual, or "continuous" or it may take place in a step-wise fashion. For example, the increase in the concentration of the halogenated anesthetic or noble gas may take place at a specified time during the subject's exposure to the halogenated anesthetic or noble gas such that the concentration of the halogenated anesthetic or noble gas is increased at least one time over the course the exposure to the halogenated anesthetic or noble gas. In one embodiment, the concentration of the halogenated anesthetic or noble gas is increased during administration such that the subject is exposed for about 1 minute or less to the highest concentration of the halogenated anesthetic or noble gas administered to the subject. In a specific example, the subject is exposed to at least one halogenated anesthetic or noble gas for about 4 minutes, with the initial concentration of the halogenated anesthetic or noble gas being at about 2% for about 3 minutes. After the third minute, the concentration of the halogenated anesthetic or noble gas is increased to from about 3.5% to about 5% for about 1 minute. In a more specific example, the subject is exposed to isoflurane or xenon for about 4 minutes, with the initial concentration of isoflurane or xenon being at about 2% for about 3 minutes. After the third minute, the concentration of the isoflurane or xenon is increased to from about 3.5% to about 5% for about 1 minute.

In another specific embodiment, the concentration of the halogenated anesthetic or noble gas is decreased during administration to the subject. The decrease can be gradual, or "continuous," or it may take place in a step-wise fashion. For example, the decrease in the concentration of the halogenated anesthetic or noble gas may take place at a specified time during the subject's exposure to the halogenated anesthetic or noble gas such that the concentration of the halogenated anesthetic or noble gas is decreased at least one time over the course the exposure to the halogenated anesthetic or noble gas. In one specific embodiment, the concentration of the halogenated anesthetic or noble gas is decreased during administration such that the subject is exposed for about 1 minute or less to the highest concentration of the halogenated anesthetic or noble gas administered to the subject. In a more specific embodiment, the concentration of isoflurane or xenon is decreased during administration such that the subject is exposed for about 1 minute or less to the highest concentration of isoflurane or xenon administered to the subject.

In yet another embodiment, the concentration of the halogenated anesthetic or noble gas is increased at least one time during the subject's exposure to the halogenated anesthetic or noble gas, and the concentration of the halogenated anesthetic or noble gas is decreased at least one time during the subject's exposure to the halogenated anesthetic or noble gas. For example, the halogenated anesthetic or noble gas may be administered to a subject beginning with a lower concentration, and the concentration is then increased at least one time during the course of the exposure. During the same exposure, the concentration would then be reduced. The invention contemplates any order of increasing or decreasing the concentration of the halogenated anesthetic or noble gas during administration. In one embodiment, the concentration of the halogenated anesthetic or noble gas is increased and decreased during administration such that the subject is exposed for about 1 minute or less to the highest concentration of the halogenated anesthetic or noble gas administered to the subject.

The invention also provides for administration of a mixture of halogenated anesthetic and oxygen to the subject. In some embodiments, the halogenated anesthetic is mixed with the oxygen in specific ratios. For example, 55% isoflurane mixed with a 95% oxygen for administration to the subject. In some embodiments, the concentration of halogenated anesthetic about 45% to about 60% while the concentration of oxygen is about 90% to about 100%.

The invention also provides pharmaceutical packs or kits comprising one or more containers filled with the halogenated anesthetic or noble gas to be administered in practicing the methods of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound.

The examples herein are for illustrative purposes only and they are not intended to limit the scope of the invention in any way.

EXAMPLES

Example 1

During studies regarding the use of obidoxime (OBD) to treat organophosphate poisoning via AChE inactivation, it was discovered that isoflurane, the anesthetic used for the intranasal delivery of OBD, was very effective as a post exposure neuroprotectant. Sprague Dawley rats (250±40 g) were exposed to lethal dose of paraoxon (4 mg/kg) and were randomly assigned to control groups or isoflurane-treated groups with a time course from about 10 minutes to about 2 hours. Isoflurane treatment involved 2% isoflurane exposure for 3 minutes followed by 5% for 1 minute in 100% oxygen. Prior to isoflurane administration, all animals exhibited at least stage 3 seizures, according to modified Racine scale until they were treated with isoflurane. Post exposure isoflurane treatment decreased seizure severity significantly with the peak effectiveness observed when isoflurane was given about 30 minutes after exposure to the AChE inactivating agent.

Animals were euthanized at 24 h following transcardial perfusion using 4% formaldehyde, and Fluoro-Jade-C staining was performed in brain slices. There were extensive neuronal degeneration in the surviving untreated control animals 24 hours after paraoxon administration, whereas the number of degenerating neurons decreased significantly in the isoflurane treated groups, with no neuronal loss at the 30 minute post-exposure treatment period. Dose-response studies indicated that exposure to about 2% isoflurane for 3 minutes following by 1 minute exposure in the ~3.5% to 5% range was effective.

Paraoxon solutions were prepared fresh by adding 10 μl of stock solution (Sigma, 1.27 g/mL) to 3 ml of ice cold PBS in a glass vial and mixing thoroughly. A lethal dose of paraoxon (4 mg/kg) was administered subcutaneously followed by intramuscular atropine sulphate (2 mg/kg) and intramuscular 2-PAM (25 mg/kg) irrespective of group. Rats were observed independently by two trained researchers for signs of seizure onset and were continuously rated for seizure severity according to a modified Racine Scale: Stage 0, no behavioral response; Stage 1, behavioral arrest, orofacial movements, chewing; Stage 2, head nodding/myoclonus; Stage 3, unilateral/bilateral forelimb clonus without rearing, straub tail, extended body posture; Stage 4, bilateral forelimb clonus plus rearing; Stage 5, rearing and falling; Stage 6, full tonic seizure.

Fixation and tissue processing were done 24 hours after paraoxon treatment. Rats were deeply anesthetized with a pentobarbital based preparation (75-100 mg/kg, i.p.) and transcardially perfused with PBS (100 ml) followed by 4% paraformaldehyde (200 ml). Brains were removed and post-fixed in 4% paraformaldehyde overnight at 4° C., then transferred to a solution of 20% sucrose in PBS. After 18 hours the sucrose solution was replaced with a fresh 20% sucrose solution and kept for 72 h, and then the tissues were frozen with dry ice before storage at −80° C. until sectioning. A 1-in-5 series of sections containing the hippocampus or amygdala was cut at 40 μm on a sliding microtome (Leica Microsystems SM2000R). Series of sections were mounted on slides (Superfrost Plus, Daigger) for FJC staining. FJC staining (Histo-Chem, Jefferson, Ark.) was used to identify irreversibly degenerating neurons in rats with and without isoflurane treatment. Mounted sections were stained with a 0.0001% solution of FJC dissolved in 0.1% acetic acid for 1 hour at 4° C. Sections were washed in distilled water, dehydrated in ethanol, cleared in xylene, and mounted with DPX. Two-dimensional sample quantitative assessments were made from 6 coronal brain sections (40 μm, both hemispheres) per animal from bregma—3.00 mm to—4.08 mm. FJC specifically stains degenerating neurons, but also stains other elements including the leptomeninges and choroid plexus. Only neurons stained by FJC were included in the neuropathological evaluations. Neuropathological evaluations were done by two independent judges blinded to the treatments. Brain regions were identified as exhibiting acute neurodegeneration when more than a few neurons in a given region were stained with FJC. This criterion was used because previous studies have reported small numbers of FJC stained neurons in brain sections obtained from vehicle controls not treated with paraoxon. Animals that showed one or more brain areas with numerous FJC stained neurons were scored as positive for acute neurodegeneration.

For statistical analyses, survival rates were compared using Fisher's Exact Test. Maximum Racine scale seizure severity rated at the different post-exposure time points was analyzed and presented as means+SEM. Racine scale data from each group was compared to control at each time point using the nonparametric Mann-Whitney U test and $p<0.05$ was considered significant.

Example 2

Figure 6:
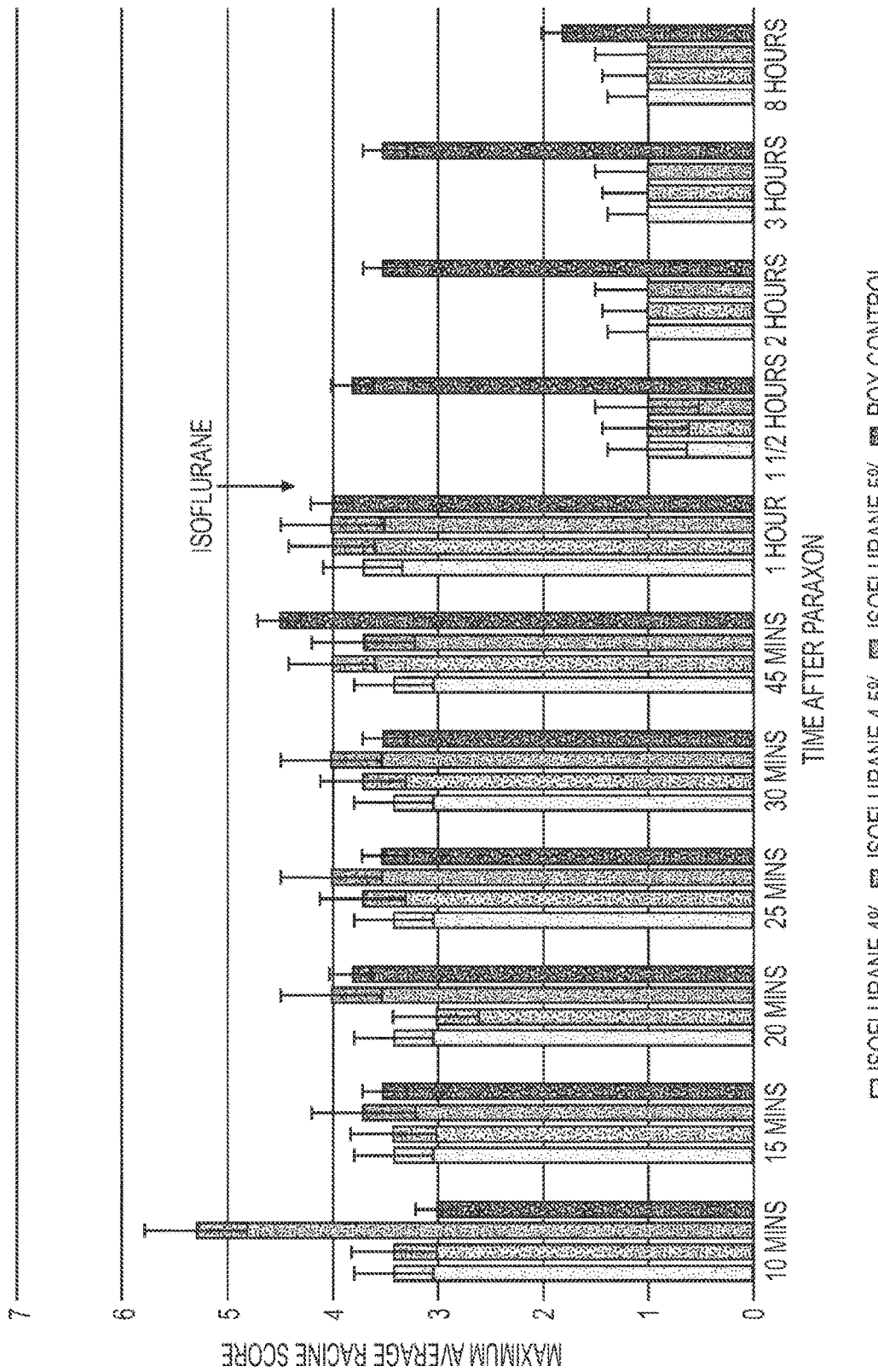
FIG. 6 depicts a Racine scale profile of seizure activity. The graph shows anticonvulsant response of isoflurane when administered 1 hour after paraoxon exposure. The bar graph shows means+SEM for seizure severity based on the Racine scale used (n=3 for each group). Each group is represented by a bar and average seizure severity scored at each time of observation. The arrow indicates the time of initiation of isoflurane administration. All groups except controls had a brief, 5 min, isoflurane administration initiated 1 hour after paraoxon and the group names indicate the concentration of isoflurane administration used (* p<0.05 in comparison to the control group that did not receive isoflurane; Mann-Whitney test).

Animals were treated 1 hour after paraoxon administration with 4%, 4.5% or 5% isoflurane in 100% oxygen for 5 minutes. Control groups were not treated with isoflurane. Animals treated with isoflurane at the 1 hour post exposure time point did not exhibit any signs of seizure activity after brief isoflurane administration and appeared to be mildly sedated for approximately 45-50 minutes after cessation of isoflurane, then displaying normal behavioral patterns afterwards (FIG. 6). Unlike the isoflurane treated groups, the untreated group continued variable seizure activity along with bleeding, lacrimation and salivation. After 24 hours the surviving untreated rats continued to show modest seizure activity and were lethargic. The animals in the isoflurane treatment groups appeared normal. In the surviving untreated control animals there was extensive neuronal degeneration 24 hours after paraoxon administration, whereas degenerating neurons were significantly reduced in the isoflurane treated groups (FIG. 6).

Example 3

Time Course Study: Animals were exposed to isoflurane in an anesthesia chamber at a concentration of 2% isoflurane (Baxter) for 3 minutes followed by 5% for 1 minute in 100% oxygen at 10, 20, 30, 45, 60 or 120 minutes after paraoxon intoxication. This pattern of isoflurane administration is based on the protocol used for anesthesia in our laboratory. The control group received paraoxon, 2-PAM and atropine sulphate, but was not treated with isoflurane.

Figure 7A:
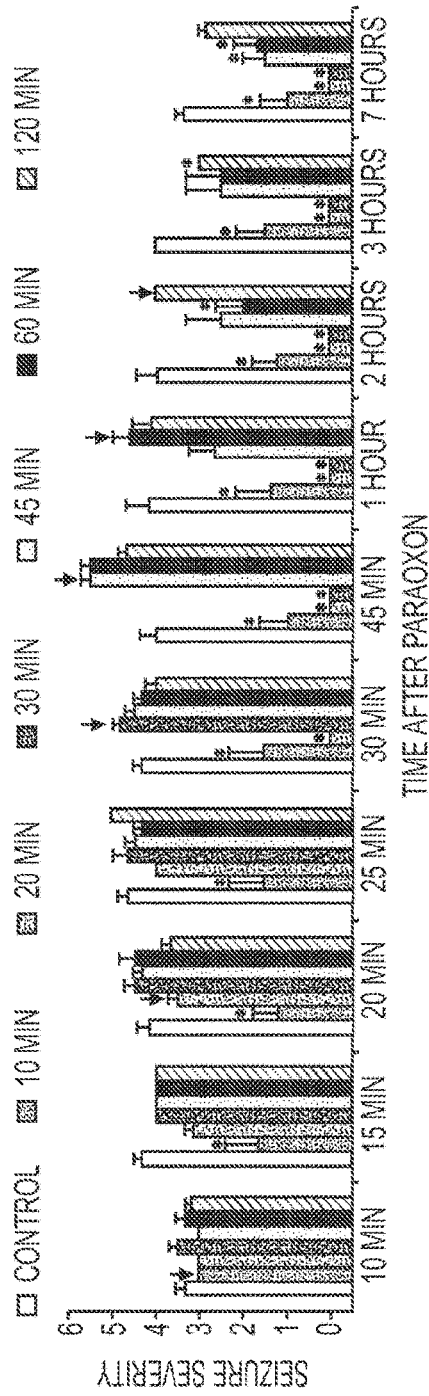
FIG. 7 depicts brief Isoflurane administration has anticonvulsant and neuroprotective properties when administered 20-30 minutes after paraoxon intoxication. The bar graph (A) shows means+SEM for seizure severity based on the modified Racine Scale (n=6 for isoflurane groups and n=7 for the untreated control group; representing the untreated animals that survived 24 hours). Each group is represented by a bar and average seizure severity was scored at each time of observation. Arrows indicate the time of initiation of brief isoflurane administration (2% for 3 minutes, 5% for 1 minute) for the treatment groups. * p<0.05 in comparison to the untreated control group (Mann-Whitney test). Fluoro Jade C staining is shown in (B) with representative photomicrographs from animals in the untreated control group (n=7) and from animals in the group that received brief isoflurane administration (n=6) initiated at 30 minutes after paraoxon. Areas shown in the photomicrographs include central thalamus (left panels), the dentate gyrus (DG) of the hippocampus (inset shows the polymorph layer) and dorsal thalamus (center panels), piriform cortex (Pir) and the medial nucleus of the amygdala (MEA; right panels). Bar=200 μm in low magnification images and 80 μm in inset images.
Figure 7B:
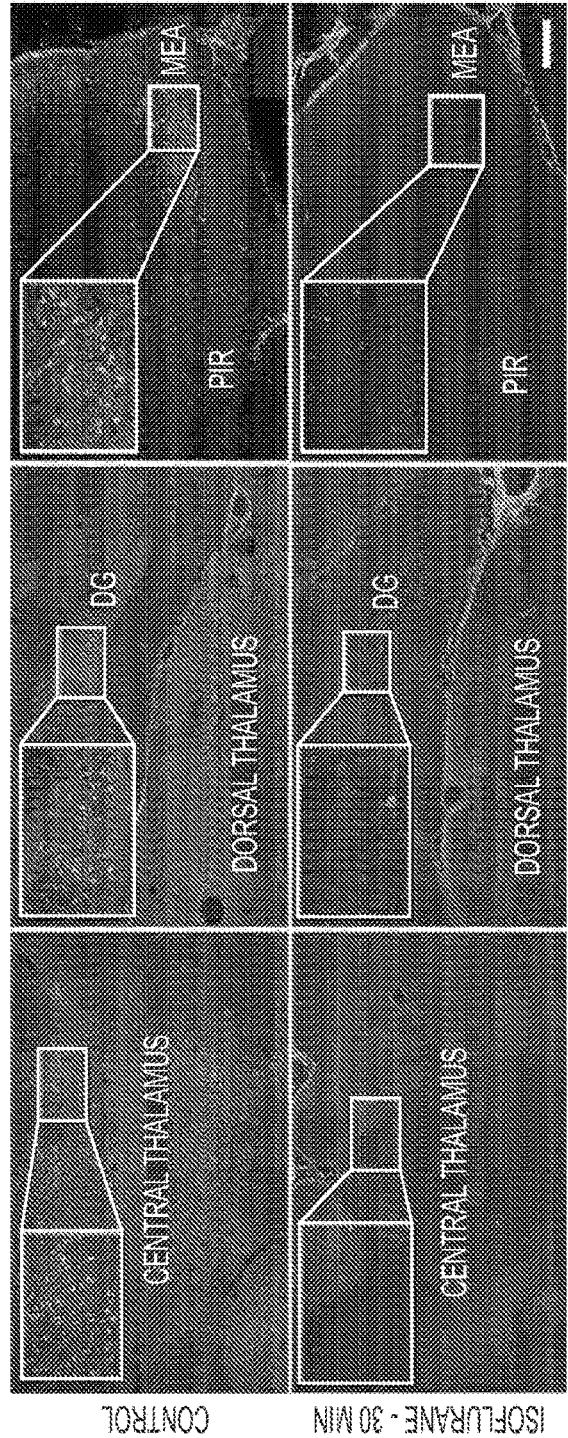

Brief administration of isoflurane (2% for 3 minutes followed by 5% for 1 minute) delivered in 100% oxygen between 10 and 120 minutes after paraoxon intoxication improved survival at all time points. The experimental groups consisted of 6 animals each, whereas the control group consisted of 11 animals to account for the expected losses due to lack of treatment. The survival rate among the animals treated with brief isoflurane administration was 100% (0/36; n=6/group) as compared to the survival rate among the untreated animals (63% (7/11); p=0.002 Fisher exact test). However, anticonvulsant and neuroprotection efficacy differed among the isoflurane-treated groups depending on the post-exposure time point of isoflurane administration. When brief isoflurane administration was initiated 10 minutes after onset of paraoxon exposure, there was a significant reduction in the average seizure severity scores (FIG. 7A) and acute neurodegeneration, characterized by positive FJC staining in several brain areas, was observed in only 2 out of 6 rats treated. When the brief isoflurane administration was initiated at 20 or 30 minutes after paraoxon intoxication, seizures were completely suppressed within 10 minute of administration and the animals appeared mildly sedated for approximately 45-50 minutes after cessation of isoflurane. Also, all animals in the 20 and 30 minute treatment groups (n=6 per group) showed no acute neurodegeneration as demonstrated by the absence of FJC positive staining in the brain 24 hours after paraoxon. In contrast, all untreated animals (n=7) showed extensive neurodegeneration in several brain areas including the dentate gyrus of the hippocampus, amygdala, parietal cortex, thalamus and piriform cortex (FIG. 7B). When brief isoflurane administration was initiated 45 or 60 minutes after paraoxon intoxication, significant reduction in seizure severity bellow stage 2 was only seen 7 hours later and neurodegeneration was observed in 5 out of 6 rats from each group. When brief isoflurane administration was initiated at 120 minutes after paraoxon, despite the statistically significant reduction in seizure severity seen 1 hour later (3 hour time point, FIG. 7A), seizure severity among those animals was maintained at or above stage 3 during all time points observed and all animals (n=6) showed neurodegeneration 24 hours after paraoxon. After 24 hours the surviving untreated rats continued to show modest seizure activity (stage 2±0.44) and were lethargic. At the 24 hour time point animals in the groups treated with isoflurane at 20 and 30 minutes after paraoxon appeared normal (stage 0) and were ambulating, eating and drinking normally.

The present results showed that when a brief 4 minute isoflurane administration (concentration of 2% for 3 minute and 3.5% or higher for 1 minute) was initiated 20 or 30 minutes after paraoxon it prevented further seizure activity and 24 hours later the animals showed normal behavior and no neurodegeneration (FIG. 7). These results support the use of isoflurane against seizures induced by OP-CTAs.

Example 4

Dose response study: The 30 minute paraoxon post-administration time point was selected for the dose response study because it was the optimal time point determined in the time-course study. Thirty minutes after onset of paraoxon exposure, animals were randomly placed in 5 groups. Control animals received no treatment. The four treated groups all received a total of 4 minutes of isoflurane administration. Two groups received the same dose throughout the 4 minute period, and two groups had the dose increased for the last 1 minute of treatment. The 4 treatment groups included; (1) 1% isoflurane for 4 minutes, (2) 2% for 4 minutes, (3) 2% isoflurane for 3 minutes followed by 3.5% for 1 minute and (4) 2% isoflurane for 3 minutes followed by 5% for 1 minute delivered in 100% oxygen.

Figure 8A:
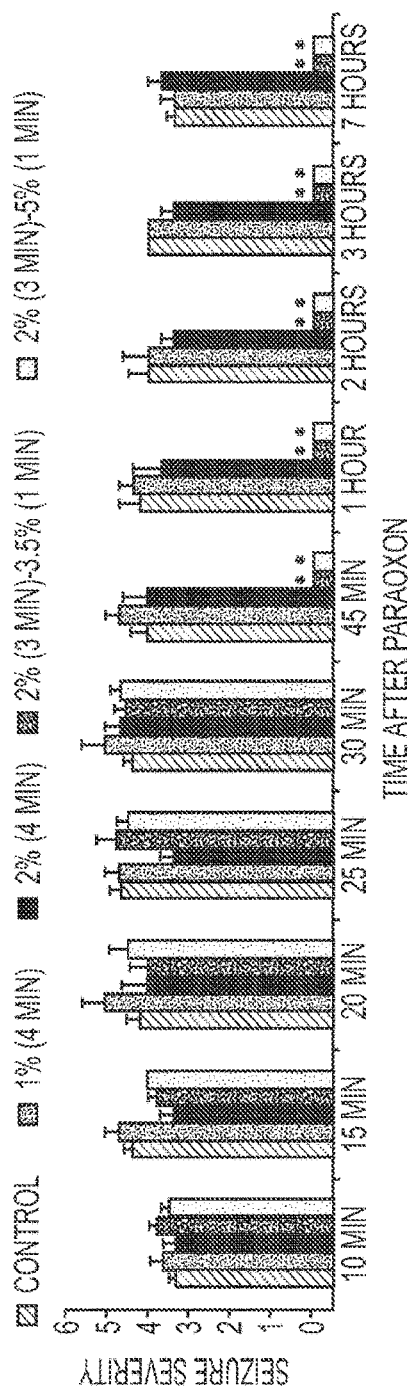
FIG. 8 depicts the anticonvulsant properties of brief Isoflurane administration are dependent on the dose when administered 30 minutes after paraoxon. The bar graph (A) shows means+SEM for seizure severity based on the Racine scale used (n=6 for each group). Each group is represented by a bar and average seizure severity scored at each time of observation. All isoflurane groups had brief (total of 4 minutes) isoflurane administration initiated 30 minutes after paraoxon and the group names indicate the concentration and duration of isoflurane administration used (* p<0.05 in comparison to the control group that did not receive isoflurane; Mann-Whitney test). FJC staining is shown in (B) with representative photomicrographs from animals (n=6 for all groups) in the 1% isoflurane group and 2% isoflurane (3 minutes)-3.5% (1 minute) group. Numerous FJC stained neurons were observed in the areas shown in the group receiving only 1% isoflurane for 4 minutes, included are the central thalamus (left panels); hippocampus, dentate gyrus (DG; inset shows the polymorph layer) and dorsal thalamus (center panels) and the piriform cortex (Pir) and medial nucleus of the amygdala (MEA; right panels). Bar=200 μm in low magnification images and 80 μm in inset images.
Figure 8B:
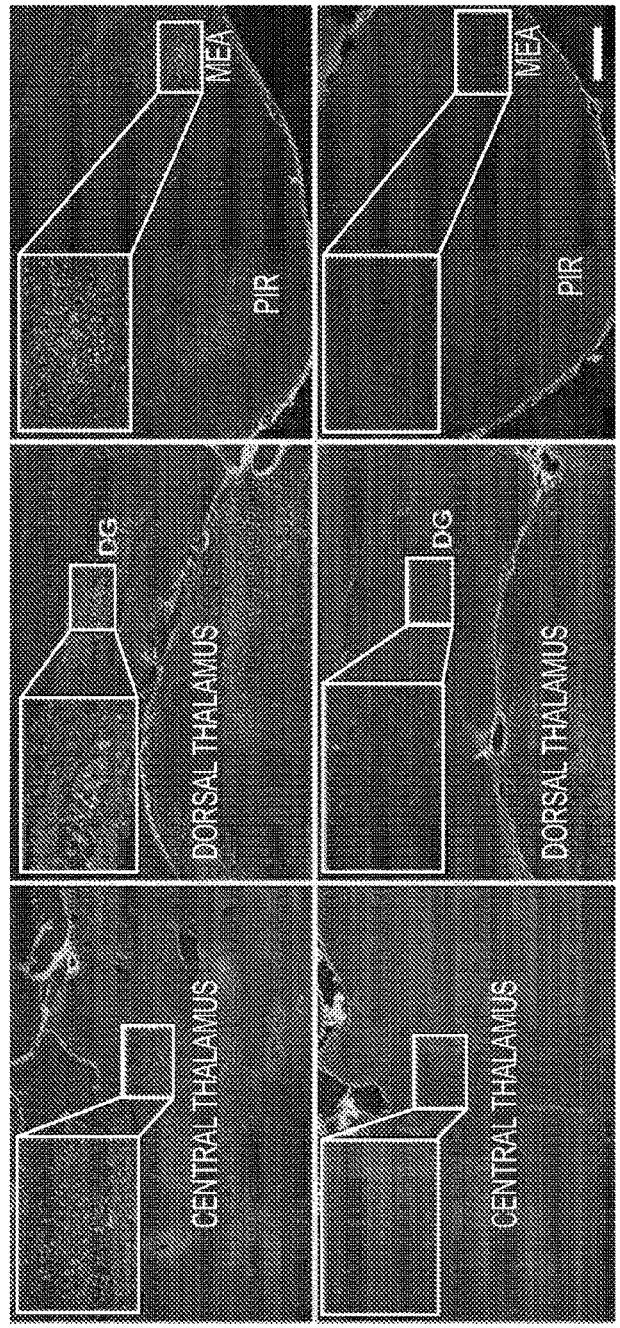

The minimal isoflurane dose that is effective to halt seizures and prevent neurodegeneration was investigated when the brief isoflurane administration was initiated 30 minutes after paraoxon. The results showed that brief administration of isoflurane stopped seizures induced by paraoxon only in the groups where concentration was increased to 3.5% or 5% for the final minute of administration (FIG. 8A). The groups that received 3.5% or 5% isoflurane for the last minute of administration showed no neurodegeneration 24 hours after intoxication, while animals that received 1% (4 minutes) or 2% (4 minutes) exhibited extensive neurodegeneration (FIG. 8B).

Isoflurane's anticonvulsant and neuroprotective actions were time and dose dependent. As with other treatments for organophosphate poisoning, when treatment is delayed 30 minutes or longer neurodegeneration is expected despite the efficacy of treatment used to prevent seizures. The minimum effective concentration of isoflurane was found to be 3.5%. Brief isoflurane administration at 1% for 4 minutes failed to prevent seizures (FIG. 8A) or neurodegeneration (FIG. 8B).

The results presented show that isoflurane is very effective as a post administration neuroprotectant by increasing survival to 100% as well as rapidly halting organophosphate poisoning-induced seizure activity and acute neurodegeneration even with relatively brief administration times. However, brief isoflurane was only fully effective in halting seizures when administered between 20 minutes and 30 minutes post-paraoxon exposure. Only partial neuroprotection was afforded at the 10, 45 and 60 minute post-exposure time points (FIG. 8). The reason for the lower effectiveness at 10 minutes is unknown, but suggests that the key pathophysiological mechanisms that are blocked by isoflurane are maximally operative in a narrow window of opportunity between 20 and 30 minutes post-paraoxon exposure.

The invention claimed is:

1. A method of reducing seizure activity, seizure severity or neurodegeneration in a subject exposed to organophosphate, the method comprising administering to the subject isoflurane or enflurane at a concentration of about 3.0% to about 7%, wherein total duration of administering is about 1 minute to about 10 minutes,
wherein the subject was exposed to the organophosphate between about 5 minutes and about 60 minutes prior to the administering of isoflurane or enflurane, and
wherein after the administering of isoflurane or enflurane, the subject exhibits a decrease in seizure activity, seizure severity or neurodegeneration as compared to a subject exposed to organophosphate but has not been administered isoflurane or enflurane.

2. The method of claim 1, wherein the isoflurane or enflurane is administered intranasally.

3. The method of claim 1, wherein the subject was exposed to the organophosphate between about 10 minutes and about 60 minutes prior to the administering of the isoflurane or enflurane.

4. The method of claim 1, wherein the organophosphate is selected from the group consisting of sarin, soman, cyclosarin, VX, paraoxon, and tabun.

5. The method of claim 1, wherein the isoflurane or enflurane is administered to the subject for about 1 to about 8 minutes.

6. The method of claim 5, wherein the isoflurane or enflurane is administered to the subject for about 2 to about 6 minutes.

7. The method of claim 5, wherein the isoflurane or enflurane is administered to the subject for about 1 minute, about 2 minutes, about 3 minutes, about 4 minutes or about 5 minutes.

8. The method of claim 1, wherein the isoflurane or enflurane is administered to the subject at a concentration of about 0.5% 3.5% to about 7%, about 4.0% to about 7%, about 4.0% to 6.0%, or about 5%.

9. The method of claim 8, wherein the isoflurane or enflurane is administered to the subject at a concentration of about 4.5% to about 5%, for about 5 minutes, and wherein the subject was exposed to the organophosphate between about 30 minutes and about 60 minutes prior to said administration.

10. The method of claim 8, wherein the concentration of the isoflurane or enflurane is increased during administration to the subject.

11. The method of claim 10, wherein the concentration of the isoflurane or enflurane is increased during administration such that the subject is exposed for about 1 minute or less to a concentration of about 5% of isoflurane or enflurane.

12. The method of claim 1, wherein the isoflurane or enflurane is co-administered with at least one oxime.

13. The method of claim 1, wherein isoflurane is administered to the subject.

14. The method of claim 1, wherein the isoflurane or enflurane is co-administered with oxygen.

15. The method of claim 14, wherein the oxygen is administered to the subject at a concentration of about 93% to about 97%.

* * * * *